(12) United States Patent
Jiang et al.

(10) Patent No.: US 11,712,204 B2
(45) Date of Patent: Aug. 1, 2023

(54) SWALLOWABLE, FOOD-BASED, DIGESTIBLE WIRELESS DEVICE FOR MEASURING GASTRIC PH

(71) Applicant: ARIZONA BOARD OF REGENTS ON BEHALF OF ARIZONA STATE UNIVERSITY, Scottsdale, AZ (US)

(72) Inventors: Hanqing Jiang, Chandler, AZ (US); Haokai Yang, Tempe, AZ (US); Wenwen Xu, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 433 days.

(21) Appl. No.: 17/100,116

(22) Filed: Nov. 20, 2020

(65) Prior Publication Data

US 2021/0068757 A1    Mar. 11, 2021

Related U.S. Application Data

(62) Division of application No. 16/280,824, filed on Feb. 20, 2019, now Pat. No. 10,842,438.

(Continued)

(51) Int. Cl.
*A61B 5/00* (2006.01)
*G01N 29/22* (2006.01)
(Continued)

(52) U.S. Cl.
CPC ............ *A61B 5/6861* (2013.01); *A61B 5/073* (2013.01); *A61B 5/14539* (2013.01);
(Continued)

(58) Field of Classification Search
None
See application file for complete search history.

(56) References Cited

U.S. PATENT DOCUMENTS 3,340,866 A  *  9/1967  Noller .................... A61B 5/073
                                                        331/65
6,998,190 B2    2/2006  Nobuta et al.
(Continued)

FOREIGN PATENT DOCUMENTS

CN          1434531 A      8/2003
CN          1938802 A      3/2007
(Continued)

OTHER PUBLICATIONS

Chinese Patent Office Action and Search Report for Application No. 201980005557.5 dated Jun. 2, 2021 (10 pages, statement of relevance included).

(Continued)

*Primary Examiner* — Michael R Bloch
(74) *Attorney, Agent, or Firm* — Michael Best & Friedrich LLP

(57) ABSTRACT

Systems and methods are presented for a swallowable pH sensor made entirely of edible and digestible materials. A substrate is provided and an electrical circuit pattern is printed on a top surface of the substrate. The electrical circuit pattern includes a plurality of interdigitated electrodes and an antenna portion. The substrate is rolled into a cylindrical form such that the interdigitated electrodes are positioned on an outermost layer of the rolled substrate. The rolling of the substrate also causes the antenna portion of the electrical circuit pattern to form into a coil shape.

10 Claims, 8 Drawing Sheets

Related U.S. Application Data

(60) Provisional application No. 62/632,545, filed on Feb. 20, 2018.

(51) Int. Cl.

| | |
|---|---|
| *G01N 29/24* | (2006.01) |
| *G01N 29/036* | (2006.01) |
| *A61B 5/07* | (2006.01) |
| *A61B 5/145* | (2006.01) |
| *A61B 5/1486* | (2006.01) |
| *B41M 3/00* | (2006.01) |

(52) U.S. Cl.
CPC ........ *A61B 5/14865* (2013.01); *A61B 5/4238* (2013.01); *B41M 3/006* (2013.01); *G01N 29/036* (2013.01); *G01N 29/222* (2013.01); *G01N 29/2481* (2013.01); *A61B 2562/125* (2013.01); *A61B 2562/166* (2013.01); *G01N 2291/014* (2013.01)

(56) References Cited

U.S. PATENT DOCUMENTS

| | | | | |
|---|---|---|---|---|
| 8,405,955 | B2 | 3/2013 | Gadkaree et al. | |
| 9,047,746 | B1 | 6/2015 | Euliano, II et al. | |
| 9,706,646 | B2 | 7/2017 | Jiang et al. | |
| 10,468,762 | B1* | 11/2019 | Knight | H01Q 1/36 |
| 2003/0165735 | A1 | 9/2003 | Nobuta et al. | |
| 2007/0103314 | A1* | 5/2007 | Geissler | A01K 11/006 |
| | | | | 340/573.1 |
| 2008/0165471 | A1 | 7/2008 | Kojima et al. | |
| 2009/0234203 | A1 | 9/2009 | Arita et al. | |
| 2011/0228447 | A1 | 9/2011 | Gadkaree et al. | |
| 2012/0130206 | A1 | 5/2012 | Vajha et al. | |
| 2012/0259376 | A1 | 10/2012 | Godden | |
| 2012/0289775 | A1* | 11/2012 | Murata | A61B 5/6861 |
| | | | | 977/734 |
| 2015/0343144 | A1* | 12/2015 | Altschul | A61B 5/4839 |
| | | | | 604/503 |
| 2016/0128589 | A1 | 5/2016 | Tabib-Azar | |
| 2016/0228061 | A1* | 8/2016 | Källbäck | A61B 5/0215 |
| 2017/0277937 | A1 | 9/2017 | Baek et al. | |
| 2017/0290151 | A1 | 10/2017 | Jiang et al. | |
| 2017/0338453 | A1 | 11/2017 | Yu et al. | |
| 2018/0180684 | A1* | 6/2018 | Govari | H05K 1/115 |
| 2018/0235881 | A1 | 8/2018 | Jiang et al. | |
| 2019/0254608 | A1 | 8/2019 | Jiang et al. | |

FOREIGN PATENT DOCUMENTS

| | | |
|---|---|---|
| CN | 101108122 A | 1/2008 |
| CN | 101273878 A | 10/2008 |
| CN | 103932676 A | 7/2014 |
| JP | 2007335443 A | 12/2007 |
| WO | WO2014113489 A1 | 7/2014 |
| WO | WO2016073584 A1 | 5/2016 |
| WO | WO2016109652 A1 | 7/2016 |
| WO | WO2017035318 A1 | 3/2017 |
| WO | WO2018208989 A1 | 11/2018 |

OTHER PUBLICATIONS

Agostoni, E. Riva, M. Giovannini, Dietary fiber in weaning foods of young children. Pediatrics 96, 1002-1005 (1995).
Agrawal, H. D. Espinosa, Giant piezoelectric size effects in zinc oxide and gallium nitride nanowires. A first principles investigation. Nano letters 11, 786-790 (2011).
Al-Hilli et al., 2009. The pH Response and Sensing Mechanism of n-Type ZnO/Electrolyte Interfaces. Sensors 9 (9), 7445.
Antipina, G. B. Sukhorukov, Remote control over guidance and release properties of composite polyelectrolyte based capsules. Adv Drug Deliv Rev 63, 716-729 (2011); published online EpubAug. 14 (10.1016/j.addr.2011.03.012).
Assaf et al., "Technical and surgical aspects of the sphenopalatine ganglion (SPG) microstimulator insertion procedure," Int. J. Oral Maxillofac. Surg., 45, 245 (2015).
Barranco, J. A. Spadaro, T. J. Berger, R. O. Becker, "In Vitro Effect of Weak Direct Current on *Staphylococcus aureus*," Clin. Orthop. Relat. Res. 100, 250-255 (1974).
Benight, C. Wang, J. B. H. Tok, Z. A. Bao, Stretchable and self-healing polymers and devices for electronic skin. Progress in Polymer Science 38, 1961-1977 (2013); published online EpubDec. (10.1016/j.progpolymsci.2013.08.001).
Ben-Menachem et al., "Vagus nerve stimulation for treatment of partial seizures: 1. A controlled study of effect on seizures. First International Vagus Nerve Stimulation Study Group," Epilepsia 35, 616-626 (1994).
Bettinger, "Materials Advances for Next-Generation Ingestible Electronic Medical Devices," Trends Biotechnol. 2015, 33, 575.
Bettinger, Z. Bao, "Organic Thin-Film Transistors Fabricated on Resorbable Biomaterial Substrates," Adv. Mater. 2010, 22, 651.
Chinese Patent Office Action for Application No. 201680061026.4 dated Mar. 5, 2019 (15 pages, English translation included).
Chinese Patent Office Action for Application No. 201680061026.4 dated Jan. 16, 2020 (17 pages, English translation included).
Co-pending U.S. Appl. No. 16/280,824, filed Feb. 20, 2019 by Hanqing Jiang et al.
Costamagna et al., A prospective trial comparing small bowel radiographs and video capsule endoscopy for suspected small bowel disease. Gastroenterology 123, 999-1005 (2002).
Cracknell, K. A. Vincent, F. A. Armstrong, Enzymes as working or inspirational electrocatalysts for fuel cells and electrolysis. Chemical Reviews 108, 2439-2461 (2008).
Davis, N. Wagle, M. D. Anderson, M. M. Warren, "Bacterial and Fungal Killing by Iontophoresis with Long-Lived Electrodes," Antimicrob. Agents Chemother. 35, 2131-2134 (1991).
Del Pozo, M. S. Rouse, J. N. Mandrekar, J. M. Steckelberg, R. Patel, "The Electricidal Effect: Reduction of *Staphylococcus* and Pseudomonas Biofilms by Prolonged Exposure to Low-Intensity Electrical Current," Antimicrob. Agents Chem. 53, 41-45 (2009).
Deuschl et al., "A randomized trial of deep-brain stimulation for parkinson's disease," N. Engl. J. Med. 355, 896-908 (2006).
Digenis, T. B. Gold, V. P. Shah, "Cross-Linking of Gelatin Capsules and Its Relevance to Their in Vitro-in Vivo Performance," J. Pharm. Sci. 1994, 83, 915.
Dorrington, D. W. Johnson, R. Brant, "The Frequency of Complications Associated With the Use of Multiple-Dose Activated Charcoal," Ann. Emergency Med. 2003, 41, 370.
Editorial Dept. of Science Pictorial Shanghai Science and Tech Press, "Experiments (Series 4)," Jun. 1958, (statement of relevance included).
EMF Portal, "Radio Frequency (10 MHz-300 GHz)," <https://web.archive.org/web/20170214032031/https://www.emf-portal.org/en/cms/page/effects-radio-frequency> webpage available at least as early as Feb. 14, 2017.
Faigel, B. R. Stotland, M. L. Kochman, T. Hoops, T. Judge, J. Kroser, J. Lewis, W. B. Long, D. C. Metz, C. O'Brien, D. Smith, and G. G. Ginsberg, 1997. Device choice and experience level in endoscopic foreign object retrieval: An in vivo study. Gastrointestinal Endoscopy 43 (4), 334.
Faigel, Douglas F. Lake, Tracy L. Landreth, Catherine C. Kelman, and Ronald J. Marler, 2016. EUS-guided portal injection chemotherapy for treatment of hepatic metastases: feasibility in the acute porcine model. Gastrointestinal Endoscopy 83 (2), 444-446.
Ferris, Conducting bio-materials based on gellan gum hydrogels. Soft Matter 5, 3430-3437 (2009).
Fu, P. Y. Liu, J. Cheng, A. S. Bhalla, R. Guo, Optical measurement of the converse piezoelectric d33 coefficients of bulk and microtubular zinc oxide crystals. Applied physics letters, (2007).
Fukada, I. Yasuda, On the piezoelectric effect of bone. Journal of the physical society of Japan 12, 1158-1162 (1957).
Gao, J. D. Xu, L. E. Locascio, and C. S. Lee, 2001. Integrated microfluidic system enabling protein digestion, peptide separation, and protein identification. Analytical Chemistry 73 (11), 2648-2655.
Gennadios, et al., "Physical Properties of Egg White—Dialdehyde Starch Films," J. Agric. Food Chem. 46, 1297-1302 (1998).

(56) References Cited

OTHER PUBLICATIONS

Goffredo et al., A Swallowable Smart Pill for Local Drug Delivery. Journal of Microelectromechanical Systems 25, 362-370 (2016).

Gontard, S. Marchesseau, J. L. Cuq, S. Guilbert, Water vapour permeability of edible bilayer films of wheat gluten and lipids. International journal of food science & technology 30, 49-56 (1995).

Halperin, S. Mutchnik, A. Agronin, M. Molotskii, P. Urenski, M. Salai, G. Rosenman, Piezoelectric effect in human bones studied in nanometer scale. Nano Letters 4, 1253-1256 (2004).

Hammock, A. Chortos, B. C. K. Tee, J. B. H. Tok, Z. A. Bao, 25th Anniversary Article: The Evolution of Electronic Skin (E-Skin): A Brief History, Design Considerations, and Recent Progress. Advanced Materials 25, 5997-6037 (2013); published online EpubNov. (10.1002/adma.201302240).

Hong, X. Zhao, J. Zhou & Z. Suo, "A theory of coupled diffusion and large deformation in polymeric gels," J. Mech. Phys. Solids 56, 1779-1793 (2008).

Huang et al., Biodegradable materials for multilayer transient printed circuit boards. Advanced Materials 26, 7371-7377 (2014).

Huggins, "Solutions of Long Chain Compounds," J. Chem. Phys. 9, 440-440 (1941).

Hwang, et al., "A Physically Transient Form of Silicon Electronics," Science 337, 1640-1644 (2012).

Hwang, et al., "Biodegradable Elastomers and Silicon Nanomembranes/Nanoribbons for Stretchable, Transient Electronics, and Biosensors," Nano Lett. 15, 2801-2808 (2015).

Hwang, et al., "High-Performance Biodegradable/Transient Electronics on Biodegradable Polymers," Adv. Mater. 26, 3905-3911 (2014).

International Preliminary Report on Patentability for Application No. PCT/US2016/048602 dated Mar. 8, 2018 (9 pages).

International Search Report and Written Opinion for Application No. PCT/US2016/048602 dated Nov. 21, 2016 (10 pages).

International Search Report and Written Opinion for Application No. PCT/US2019/18785 dated Apr. 30, 2019 (14 pages).

Irimia-Vladu, ""Green" electronics: biodegradable and biocompatible materials and devices for sustainable future," Chem. Soc. Rev. 2014, 43, 588.

Irimia-Vladu, E. D. Glowacki, G. Voss, S. Bauer, N. S. Sariciftci, "Green and biodegradable electronics," Mater. Today 15, 340-346 (2012).

Irimia-Vladu, et al., "Biocompatible and Biodegradable Materials for Organic Field-Effect Transistors," Adv. Funct. Mater. 20, 4069-4076 (2010).

Irimia-Vladu, et al., "Indigo—A Natural Pigment for High Performance Ambipolar Organic Field Effect Transistors and Circuits," Adv. Mater. 24, 375 (2012).

Kahlon, M. Chapman, G. Smith, In vitro binding of bile acids by spinach, kale, brussels sprouts, broccoli, mustard greens, green bell pepper, cabbage and collards. Food chemistry 100, 1531-1536 (2007).

Kang, et al., "Biodegradable Thin Metal Foils and Spin-On Glass Materials for Transient Electronics," Adv. Funct. Mater. 25, 1789-1797 (2015).

Karimi, M. Navidbakhsh, H. Yousefi & M. Alizadeh, "An experimental study on the elastic modulus of gelatin hydrogels using different stress-strain definitions," Journal of Thermoplastic Composite Materials, 2014.

Kavanagh, T. Menand & K. A. Daniels, "Gelatine as a crustal analogue: Determining elastic properties for modelling magmatic intrusions," Tectonophysics 582, 101-111 (2013).

Khang, H. Q. Jiang, Y. Huang, J. A. Rogers, A stretchable form of single-crystal silicon for high-performance electronics on rubber substrates. Science 311, 208-212 (2006); published online EpubJan. (10.1126/science.1121401).

Kim, J. H. Ahn, W. M. Choi, H. S. Kim, T. H. Kim, J. Z. Song, Y. G. Y. Huang, Z. J. Liu, C. Lu, J. A. Rogers, Stretchable and foldable silicon integrated circuits. Science 320, 507-511 (2008); published online EpubApr. (10.1126/science.1154367).

Kim, R. Ghaffari, N. S. Lu, J. A. Rogers, "Flexible and stretchable electronics for biointegrated devices," in Annual Review of Biomedical Engineering, vol. 14, M. L. Yarmush, Ed. (2012), vol. 14, pp. 113-128.

Kim, S. Yun, Z. Ounaies, Discovery of cellulose as a smart material. Macromolecules 39, 4202-4206 (2006).

Kim, S.-E. Chun, J. Whitacre, C. J. Bettinger, "Self-deployable current sources fabricated from edible materials," J. Mater. Chem. B 1, 3781-3788 (2013).

Kim, W. Wu, S. E. Chun, J. F. Whitacre, C. J. Bettinger, Catechol-Mediated Reversible Binding of Multivalent Cations in Eumelanin Half-Cells. Advanced Materials 26, 6572-6579 (2014).

Kim, W. Wu, S.-E. Chun, J. F. Whitacre, C. J. Bettinger, "Biologically derived melanin electrodes in aqueous sodium-ion energy storage devices," Proc. Natl. Acad. Sci. U.S.A. 110, 20912-20917 (2013).

Koziolek et al., Investigation of pH and temperature profiles in the GI tract of fasted human subjects using the Intellicap® system. Journal of pharmaceutical sciences 104, 2855-2863 (2015).

Kroin et al., Long-term testing of an intracranial pressure monitoring device. Journal of neurosurgery 93, 852-858 (2000).

Król, A. Jarmoluk, "The effects of using a direct electric current on the chemical properties of gelatine gels and bacterial growth," J. Food Eng. 170, 1-7 (2016).

Lee, J. Shim, and H. G. Lee, 2004. Mechanical properties of gellan and gelatin composite films. Carbohydrate Polymers 56 (2), 251-254.

Li, D. Young, K. Xiang, W. C. Carter, Y.-M. Chiang, "Towards High Power High Energy Aqueous Sodium-Ion Batteries: The NaTi2(PO4)3/Na0.44MnO2 System," Adv. Energy Mater. 3, 290-294 (2013).

Li, R. S. Yang, M. Yu, F. Bai, C. Li, and Z. L. Wang, 2008. Cellular Level Biocompatibility and Biosafety of ZnO Nanowires. Journal of Physical Chemistry C 112 (51), 20114-20117.

Li, V. Kothari, B. S. Terry, Design and Preliminary Experimental Investigation of a Capsule for Measuring the Small Intestine Contraction Pressure. IEEE Transactions on Biomedical Engineering 62, 2702-2708 (2015).

Lipomi, M. Vosgueritchian, B. C. K. Tee, S. L. Hellstrom, J. A. Lee, C. H. Fox, Z. N. Bao, Skin-like pressure and strain sensors based on transparent elastic films of carbon nanotubes. Nature Nanotechnology 6, 788-792 (2011); published online EpubDec. (10.1038/nnano.2011.184).

Lu, T. Chen, "Application of egg white and plasma powders as muscle food binding agents," J. Food Eng. 42, 147-151 (1999).

Marino, R. O. Becker, Piezoelectricity in hydrated frozen bone and tendon. Nature 253, 42 (1975).

Matsunaga, et al., "Disinfection of Drinking Water by Using a Novel Electrochemical Reactor Employing Carbon-Cloth Electrodes," Appl. Environ. Microbiol. 58, 686-689 (1992).

Matsunaga, S. Nakasono, S. Masuda, "Electrochemical sterilization of bacteria adsorbed on granular activated carbon," FEMS Microbiol. Lett. 72, 255-259 (1992).

Munoz, G. Alici, W. Li, A review of drug delivery systems for capsule endoscopy. Adv Drug Deliv Rev 71, 77-85 (2014).

Nathan, S. Center, C.-y. Wu, W. Keller, An implantable synchronous pacemaker for the long term correction of complete heart block. The American journal of cardiology 11, 362-367 (1963).

Neuvonen, "Clinical Pharmacokinetics of Oral Activated Charcoal in Acute Intoxications," Clin. Pharmacokinet. 1982, 7, 465.

Neuvonen, K. T. Olkkola, "Oral Activated Charcoal in the Treatment of Intoxications," Med. Toxicol. Adverse Drug Exper. 1988, 3, 33.

Ofner, Y. E. Zhang, V. C. Jobeck, B. J. Bowman, "Crosslinking Studies in Gelatin Capsules Treated with Formaldehyde and in Capsules Exposed to Elevated Temperature and Humidity," J. Pharm. Sci. 2001, 90, 79.

Parker, P. Domachuk, J. Amsden, J. Bressner, J. A. Lewis, D. L. Kaplan, F. G. Omenetto, Biocompatible silk printed optical waveguides. Advanced Materials 21, 2411-2415 (2009).

Peng et al., Diagnosing lung cancer in exhaled breath using gold nanoparticles. Nature nanotechnology 4, 669-673 (2009).

(56) References Cited

OTHER PUBLICATIONS

Pickup, H. Keen, "Continuous Subcutaneous Insulin Infusion at 25 Years," Diabetes Care 25, 593-598 (2002).

Qureshi, Current and future applications of the capsule camera. Nature reviews drug discovery 3, 447-450 (2004).

Ramuz, B. C. K. Tee, J. B. H. Tok, Z. N. Bao, Transparent, Optical, Pressure-Sensitive Artificial Skin for Large-Area Stretchable Electronics. Advanced Materials 24, 3223-3227 (2012); published online EpubJun. (10.1002/adma.201200523).

Reinish, A. S. Nowick, Piezoelectric properties of bone as functions of moisture content. (1975).

Rogers, T. Someya, Y. G. Huang, Materials and Mechanics for Stretchable Electronics. Science 327, 1603-1607 (2010); published online EpubMar. (10.1126/science.1182383).

Rossi, C. L. Dias, E. M. Donato, L. A. Martins, A. M. Bergold, and P. E. Froeehlich, 2007. Development and validation of dissolution test for ritonavir soft gelatin capsules based on in vivo data. International Journal of Pharmaceutics 338 (1-2), 119-124.

Sandvik, B. R. McLeod, A. E. Parker, P. S. Stewart, Direct electric current treatment under physiologic saline conditions kills *Staphylococcus epidermidis* biofilms via electrolytic generation of hypochlorous acid. PloS one 8, (2013).

Schubert, 2014. Gastric secretion. Current Opinion in Gastroenterology 30 (6), 578-582.

Siegel, K. Church, G. Schmidt, "Gel Structure of Nonmeat Proteins as Related to Their Ability to Bind Meat Pieces," J. Food Sci. 44, 1276-1279 (1979).

Tamborlane, R. S. Sherwin, M. Genel, P. Felig, "Reduction to normal of plasma glucose in juvenile diabetes by subcutaneous administration of insulin with a portable infusion pump," N. Engl. J. Med. 300, 573-578 (1979).

Tao, D. L. Kaplan, F. G. Omenetto, "Silk Materials—A Road to Sustainable High Technology," Adv. Mater. 2012, 24, 2824.

Vanin, P. J. A. Sobral, F. C. Menegalli, R. A. Carvalho, and Amqb Habitante, 2005. Effects of plasticizers and their concentrations on thermal and functional properties of gelatin-based films. Food Hydrocolloids 19 (5), 899-907.

Vosgueritchian, D. J. Lipomi, Z. A. Bao, Highly Conductive and Transparent PEDOT:PSS Films with a Fluorosurfactant for Stretchable and Flexible Transparent Electrodes. Advanced Functional Materials 22, 421-428 (2012); published online EpubJan. (10.1002/adfm.201101775).

Wang, W. Xu, P. Chatterjee, C. Lv, J. Popovich, Z. Song, L. Dai, M. Y. S. Kalani, S. E. Haydel, H. Jiang, Food-Materials-Based Edible Supercapacitors. Advanced Materials Technologies 1, (2016).

Welz, C. M. Ofner, "Examination of Self-Crosslinked Gelatin as a Hydroggel for Controlled Release," J. Pharm. Sci. 1992, 81, 85.

Wu, A. Mohamed, J. F. Whitacre, "Microwave Synthesized $NaTi_2(PO_4)_3$ as an Aqueous Sodium-Ion Negative Electrode," J. Electrochem. Soc. 160, A497-A504 (2013).

Wu, M. Khdour, P. Apsangi, and H. Yu, 2017. High-Frequency Magnetic Thin-Film Inductor Integrated on Flexible Organic Substrates. IEEE Transactions on Magnetics 53 (11), 1-7.

Xu et al. "Food Based Edible and Nutritive Electronics" Advanced Materials Technologies, 2017 (10.1002/admt.201700181).

Xu, Y. H. Zhang, L. Jia, K. E. Mathewson, K. I. Jang, J. Kim, H. R. Fu, X. Huang, P. Chava, R. H. Wang, S. Bhole, L. Z. Wang, Y. J. Na, Y. Guan, M. Flavin, Z. S. Han, Y. G. Huang, J. A. Rogers, Soft Microfluidic Assemblies of Sensors, Circuits, and Radios for the Skin. Science 344, 70-74 (2014); published online EpubApr. (10.1126/science.1250169).

Yan, Q. Wang, T. Wei, Z. Fan, "Recent Advances in Design and Fabrication of Electrochemical Supercapacitors with High Energy Densities," Adv. Energy Mater. 2014, 4, 4.

Yin, et al., "Materials, Designs, and Operational Characteristics for Fully Biodegradable Primary Batteries," Adv. Mater. 26, 3879-3884 (2014).

Zhang, X. Zhao, "Carbon-based materials as supercapacitor electrodes," Chem. Soc. Rev. 38, 2520-2531 (2009).

\* cited by examiner

SWALLOWABLE, FOOD-BASED, DIGESTIBLE WIRELESS DEVICE FOR MEASURING GASTRIC PH

CROSS-REFERENCE TO RELATED APPLICATIONS

This application is a divisional of U.S. patent application Ser. No. 16/280,824, filed on Feb. 20, 2019, which claims the benefit of U.S. Provisional Patent Application No. 62/632,545, filed Feb. 20, 2018, entitled "SWALLOWABLE, FOOD-BASED, DIGESTIBLE WIRELESS DEVICE FOR MEASURING GASTRIC pH," the entire contents of which are incorporated herein by reference.

BACKGROUND

On-person electronics, as either wearable or implantable systems, have an increasingly significant role in healthcare monitoring, diagnosis and therapy. Progress in the development of healthcare devices has been boosted by dramatic advances in electronic materials—with expansion of the form factor and constituents of electronic materials as well as with the advent of flexible, stretchable, and transient systems. Skin-based systems are able to detect variables such as heart rate, temperature, and sweat-based body constituents. Implantable systems can be more robust, but they are invasive and present a risk of infection, bleeding, and a need for surgical recovery in the event of a malfunction.

One body domain that has only been partially explored to administer electronics has been the gastrointestinal (GI) tract. The GI tract is a primary interface between the external environment and the internal milieu, affording tremendous surface area for device residence and monitoring of a wide range of health and disease conditions and states. To date a limited number of devices have been fabricated for GI use. These devices may, for example, be swallowed whole or implanted via endoscopy.

These include capsule endoscopes (PillCam™, Medtronic, Minneapolis, Minn.) and capsules to measure GI motility and pH (SmartPill™, Medtronic, Minneapolis, Minn.). These devices are not biodegradable and run the risk of causing bowel obstructions if they become entrapped in areas of stenosis. They are also relatively expensive. For these reasons they are not suitable for repeated administration over time. Acid peptic disorders are extremely common and are treated with acid suppression medications that carry risk. There is a critical need to be able to measure gastric pH repeatedly over time to diagnose these disorders, objectively monitor response to therapy in order to use the lowest effective dose of medicine, and in a safer and more cost effective manner than currently available.

Currently, to measure gastric pH the options are limited to placing a naso-gastric tube (invasive and uncomfortable), performing upper endoscopy with gastric aspirate (invasive and expensive) or administering the SmartPill® (Given Imaging). The SmartPill® is a non-biodegradable swallowable electronic device capable of wirelessly transmitting pH information after ingestion. It is expensive and can become retained within the intestine if there are any stenoses or blockages. SmartPill® is made by MEMS (Micro-Electro-Mechanical Systems)-based processes that use materials (e.g., Cu) foreign to the GI tract. Because of the non-edible materials used in the ingestible electronics, there are safety concerns. A digestible device made of inexpensive components would be safer and potentially less expensive.

Accordingly, real-time measurement of pH values in the GI tract has significant medical importance. Patients with acid secretory disorders (gastroesophageal reflux disease, peptic ulcer disease, Zollinger-Ellison syndrome) would benefit from regular intermittent monitoring of gastric pH particularly if this could be done inexpensively and safely.

SUMMARY

It was recently discovered that food-based materials can be used to build electronics. Functional components, such as resistors and antennas, all made of food-materials and, on a limited basis, non-toxic levels of edible metals (e.g., gold) have been demonstrated. Moreover, a pH sensor made of edible components was demonstrated that can measure the pH values and wirelessly transmit the signal passively. Herein described is the use of edible and digestible materials to develop a miniaturized pH sensor that can survive in the acidic gastric environment and utilize smart phone functionality to wirelessly read the data from the edible pH sensor (see FIG. 1). Design, fabrication, characterizations in both the lab environments and animal experiments will be performed.

In one embodiment, the disclosure provides a system for pH sensing that includes a planar structure rolled into a cylindrical form and an electrical circuit pattern formed on the surface of the planar structure. The electrical circuit pattern includes an antenna portion formed into a coil by rolling of the planar structure into the cylindrical form. The electrical circuit pattern also includes a plurality of interdigitated electrodes that are at least partially positioned on an exterior of the rolled planar structure in the cylindrical form.

In another embodiment, the disclosure provides a method of assembling a swallowable pH sensor. A substrate is provided and an electrical circuit pattern is printed on a top surface of the substrate. The electrical circuit pattern includes a plurality of interdigitated electrodes and an antenna portion. The substrate is rolled into a cylindrical form such that the interdigitated electrodes are positioned on an outermost layer of the rolled substrate. The rolling of the substrate also causes the antenna portion of the electrical circuit pattern to form into a coil shape. The swallowable pH sensor is made entirely of edible and digestible materials.

In some embodiments, the disclosure provides a digestible pH sensor comprising a cylindrically formed planar structure, which includes a plurality of electrodes comprising gold (Au)—ZnO, an antenna comprising Au for wirelessly transmitting signals, and an edible capacitor.

In other embodiments, the disclosure provides a method of a digestible pH sensor comprising a cylindrically formed planar structure, which includes a plurality of electrodes comprising gold (Au) and a metal oxide, an antenna comprising Au for wirelessly transmitting signals, and an edible capacitor.

In a further embodiment, the disclosure provides a system for measuring parameters of a gastrointestinal tract. The system comprises a digestible sensor including an antenna, the digestible sensor formed as a cylinder, and a device configured to read data from the digestible sensor, the device exterior to the gastrointestinal tract.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
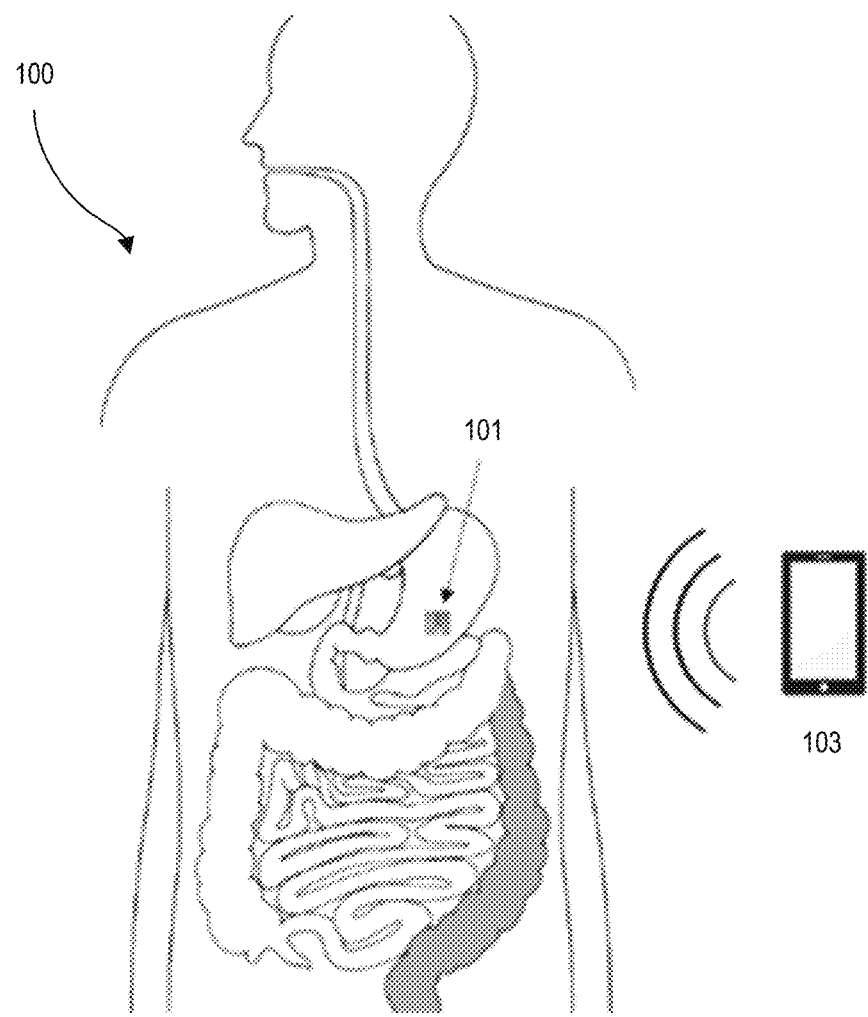
FIG. 1 schematically illustrates an edible and digestible pH sensor in wireless communication with an external device according to one embodiment.

FIG. 1 illustrates an example of a pH sensor system. A patient 100 swallows a pH sensor capsule 101, which travels through the patient's digestive system. In the example of FIG. 1, the pH sensor capsule 101 has reached the patient's stomach. An external device 103 (for example, a Smart Phone or another device) is configured to wirelessly communicate with the pH sensor capsule 101 in order to read the pH level of the environment in which the pH sensor capsule 101 is currently located. For example, when the capsule 101 is positioned in the stomach of the patient 100 (as illustrated in FIG. 1), the external device 103 is able to determine the gastric pH of the stomach.

Figure 2C:
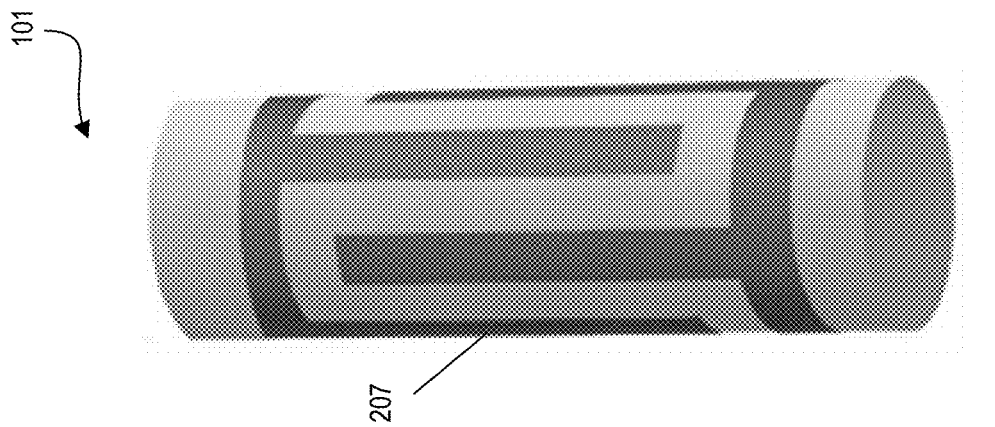
FIG. 2C is a perspective view of the pH sensor of FIG. 2A in its filled "rolled" form.
Figure 2A:
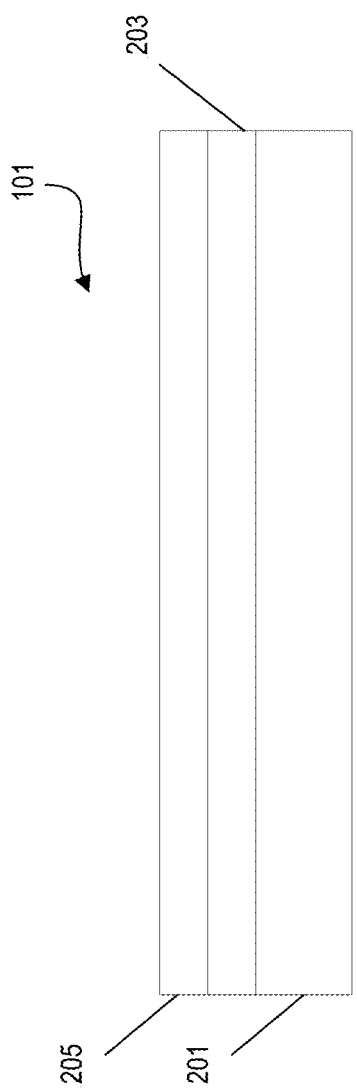
FIG. 2A is a cross-sectional diagram of an unrolled pH sensor from the embodiment of FIG. 1.

In some implementations, the pH sensor capsule 101 is constructed by printing (or otherwise depositing) an electric circuit pattern 203 on a substrate 201 (as illustrated in FIG. 2A) and rolling the substrate into a capsule form (as illustrated in FIG. 2C). As shown in FIG. 2A, in some implementations, a coating layer 205 is deposited on top of the electrical circuit pattern 203 after the electrical circuit pattern 203 is printed on the substrate 201. Accordingly, the electrical circuit pattern 203 is positioned between the substrate 201 and the coating layer 205.

Figure 2B:
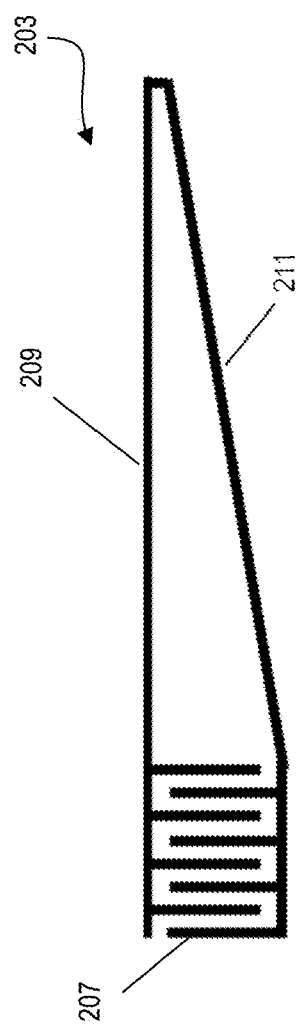
FIG. 2B is an overhead view of one example of a printed circuit of the pH sensor of FIG. 2A.

FIG. 2B illustrates one example of a type of electrical circuit pattern 203 that may be printed on the substrate 201. In this example, the electrical circuit pattern 203 includes a plurality of interdigitated linear electrodes 207. As discussed in further detail below, the electrodes 207 are positioned to contact or chemically interface with the biological environment when the capsule is swallowed. A first set of electrodes is coupled to a first node (shown at the top of FIG. 2B) while a second set of electrodes is coupled to a second node (shown at the bottom of FIG. 2B). The printed circuit pattern further includes a linear top portion 209 that extends from the first set of electrodes in a direction perpendicular to the linear electrodes 207 and an angled portion 211 that extends from the second set of electrodes. The angled portion 211 in the example of FIG. 2B contacts a distal end of the linear top portion 209 at an angle to form a substantially triangular shape in the printed circuit pattern.

After the electrical circuit pattern 203 is printed on the substrate 201 and is covered by the coating layer 205, the pH sensor 101 is rolled into a cylindrical shaped form as illustrated in FIG. 2C. In the example of FIG. 2C, the substrate 201 is rolled with the electrical circuit pattern 203 positioned on the exterior side and, as a result, at least some of the electrodes 207 are visible on the exterior surface of the rolling capsule 101 in FIG. 2C. Furthermore, when the substrate 201 is rolled, the angled portion 211 of the electrical circuit pattern 203 is also rolled into a coil inside the capsule 101. As discussed in further detail below, when the angled portion 211 is rolled into a coil, it operates as an inductor coil that can be used for wireless communication with an external device.

Figure 3:
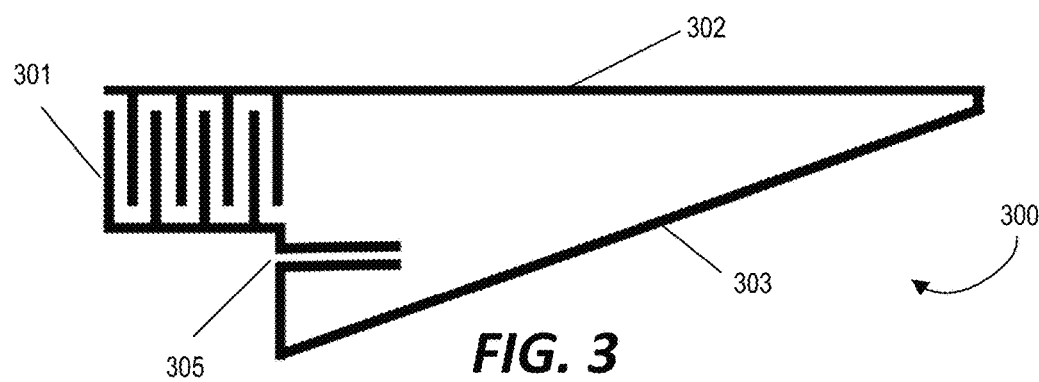
FIG. 3 is a second example of a printed circuit pattern for use in a pH sensor of FIG. 2A.

The electrical circuit pattern 203 illustrated in FIG. 2B is only one example of a circuit pattern that, when rolled into capsule form, can operate as a wireless pH sensor. FIGS. 3-6 illustrate just a few other possible printed circuit patterns that may be utilized to implement a wireless pH sensor when rolled into a capsule form. In the example of FIG. 3, a series of interdigitated linear electrodes 301 are again coupled to a substantially triangular circuit pattern that includes a linear portion 302 and an angled portion 303. However, the electrical circuit pattern 300 also includes a capacitor 305 positioned between the electrodes and the angled portion 303. When a substrate printed with the pattern 300 is rolled, the angled portion 303 forms an inductor coil and a capacitor 305 is positioned between the electrodes and the bottom of the resulting inductor coil. In the final rolled capsule, the electrodes 301 do not overlap with the capacitor 305.

Figure 4:
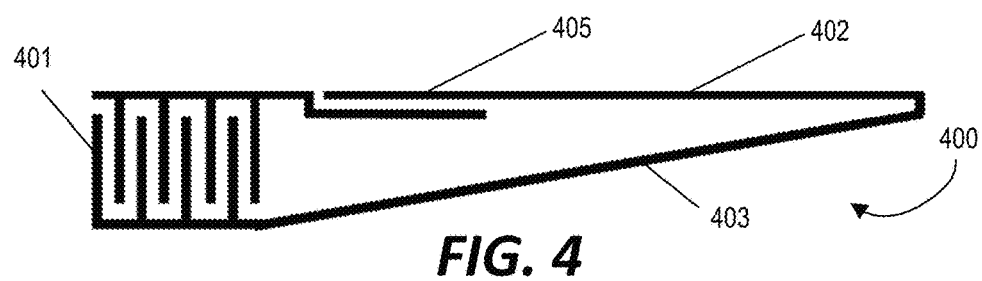
FIG. 4 is a third example of a printed circuit pattern for use in the pH sensor of FIG. 2A.

In the example of FIG. 4, the electrical circuit pattern 400 includes a set of interdigitated liner electrodes 401 coupled to both a linear portion 402 and an angled portion 403. However, in the example of FIG. 4, the capacitor 405 is positioned between the electrodes and the linear portion 402. Accordingly, when a substrate printed with the electrical circuit pattern 400 of FIG. 4 is rolled into a capsule form, the angled portion 403 forms an inductor coil and the capacitor 405 is positioned at the top of the capsule on the inner layers below the electrodes 401.

Figure 5:
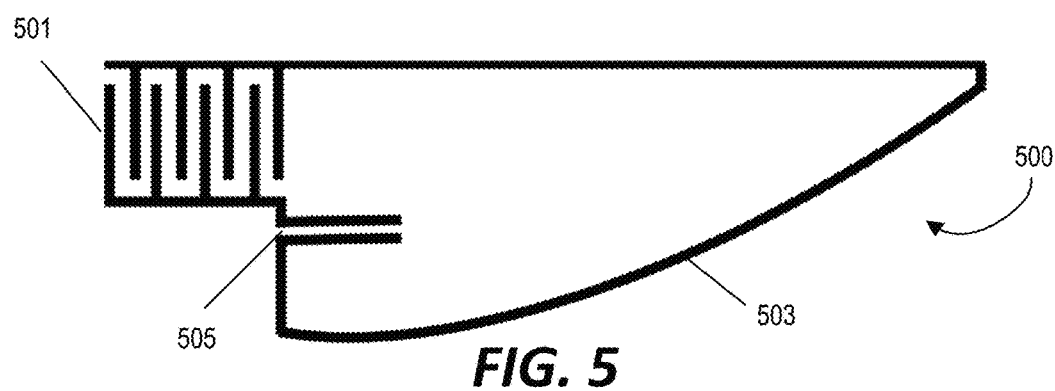
FIG. 5 is a fourth example of a printed circuit pattern for use in the pH sensor of FIG. 2A.
Figure 6:
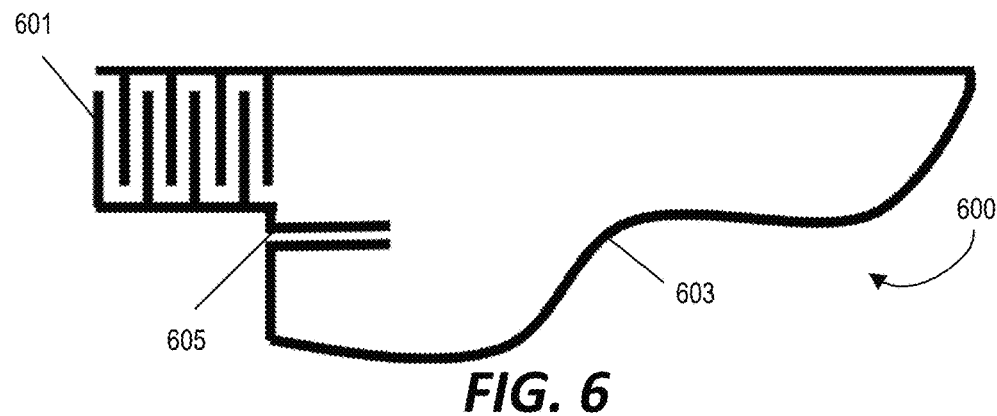
FIG. 6 is a fifth example of a printed circuit pattern for use in the pH sensor of FIG. 2A.

In the examples of FIGS. 5 and 6, the electrical circuit patterns 500, 600 also provide a set of liner interdigitated electrodes 501, 601 and a capacitor 505, 605 arranged similar to the electrical circuit pattern 300 of FIG. 3. However, instead of an "angle portion" that extends linearly to form the substantially triangular pattern, these examples include an angled portion 503, 603 that is curved. When a substrate printed with the electrical circuit pattern 500, 600 is rolled, the curved angled portion 503, 603 still forms an inductor coil.

The size, shape, and design of the electrical circuit pattern can be adjusted or "tuned" for various different particular applications. For example, the sensitivity of the pH sensor can be adjusted by changing the number, size, and/or spacing of the interdigitated electrodes. Performance can also be adjusted by changing the angle of the triangular portion of the electrical circuit pattern (i.e., the angle at which the "angled portion" contacts the liner portion), the shape of the angled portion, and the size/position of the capacitor. For example, as discussed above, the shape of the angled portion of the electrical circuit pattern can include a straight line (as in FIGS. 2B, 3, and 4) or a curved line (as in FIGS. 5 and 6).

The angle between the angled portion and the linear portion can be varied, for example, by adjusting the length of the linear portion and the angled portion and/or adjusting the distance between the terminal nodes of the first set of electrodes and the second set of electrodes. The angle can also be adjusted by varying the size of an offset between the terminal node of the second set of electrodes and a first end of the angled portion. For example, in the examples of FIGS. 2B and 4, the angled portion 203, 403 extends directly from the terminal node of the second set of electrodes. In contrast, in FIGS. 3, 5, and 6, the beginning of the angled portion 303, 503, 603 is offset from the terminal node of the second set of electrodes. In these examples, a capacitor 305, 505, 605 is positioned on the offset between the electrodes and the angled portion 303, 503, 603. However, in some implementations, an offset can be included to increase the angle between the angled portion and the linear portion without including a capacitor on the offset. It is also noted that, although the electrical circuit pattern of FIG. 2B does not include a separate "capacitor" component, the interdigitated electrodes 207 can in some cases also function as a capacitor.

In some implementations, the entire pH sensor 101 is constructed of digestible and benign materials to resolve the incompatibility of traditional semiconductor materials with the GI tract. Different from the existing microelectromechanical systems (MEMS)-based ingestible electronics (e.g., SmartPill™) that use materials (e.g., Cu) foreign to the GI tract, the swallowable digestible pH sensors described herein have unprecedented merits that are lacking with the current ingestible electronics as they constitute edible materials, from the packaging substrate (e.g., gelatin) to the functional materials (e.g., ZnO), which are digestible and benign and therefore significantly reduce and largely eliminate safety concerns. The digestible pH sensor offers unprecedented advancement on the techniques for basic science discovery and understanding of the physiologic and pathologic characterizations of the gastric environment in a cost-effective manner. This can be used in many scenarios: this would allow for repeated administrations over time or even within the same day; this would be useful for monitoring response to therapy such as for patients on acid suppression therapy with proton pump inhibitors. More importantly, this exploratory research opens the door for edible and digestive electronics with vast applications in monitoring and diagnosing diseases related to the GI system.

Figure 7A:
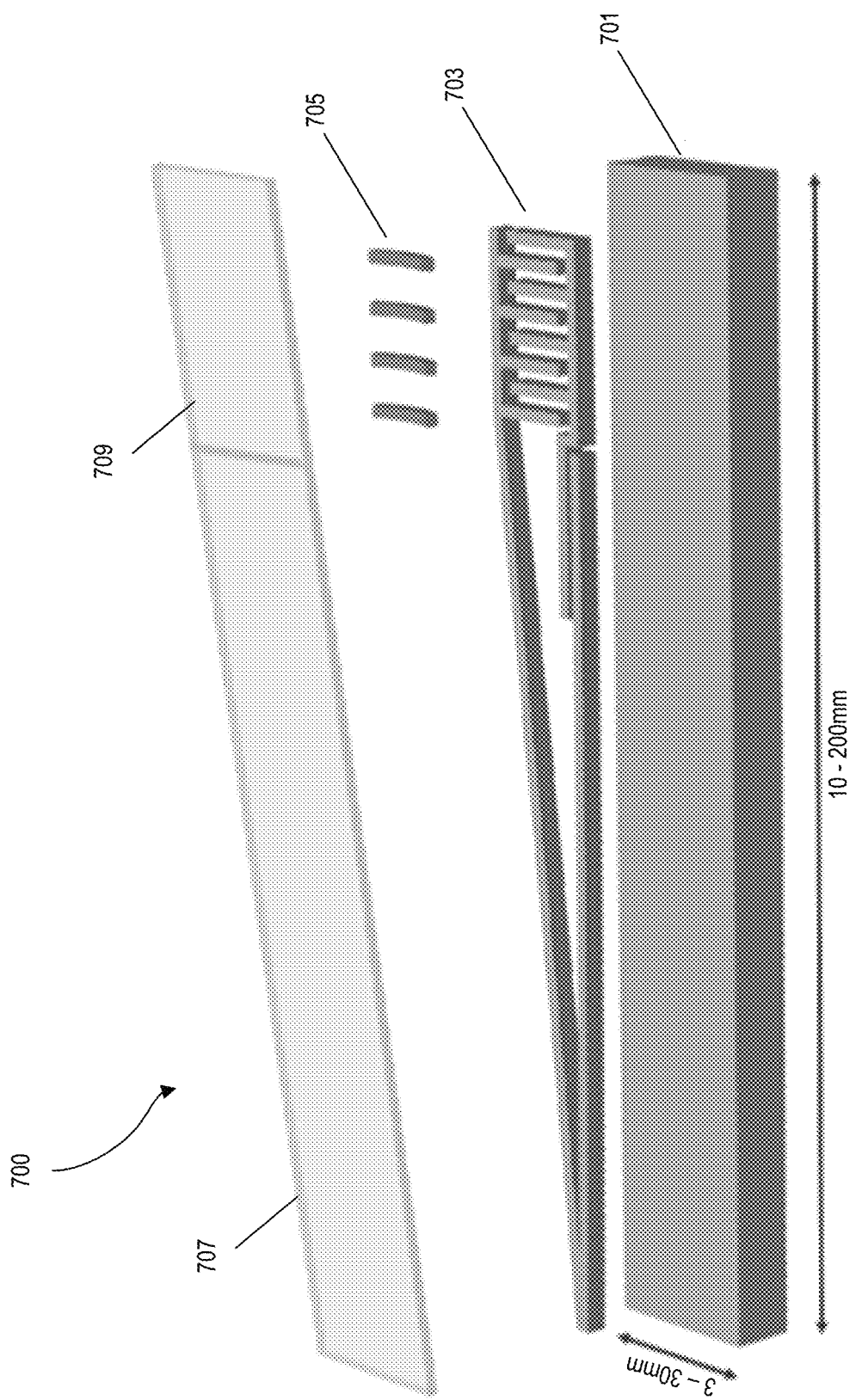
FIG. 7A is an exploded view of another example of a pH sensor using the printed circuit pattern of FIG. 4.

FIG. 7A illustrates another example of the construction of an edible pH sensor 700. The substrate 701 is formed of an edible material such as, for example, gelatin/glycerol, a Edragit film, crosslinked alginate film, starch film, Konjac-Mannan film, crosslinked chitosan film, PLA, PGA, PLGA, or other edible and biodegradable film materials. The electrical circuit pattern 703 is printed onto the surface of the substrate 701 using gold or another material that is both edible and electrically conductive. In some implementations, a material with pH-sensitive impedance properties (e.g., ZnO, $Fe_3O_4$, $WO_2$, or another edible metal or metal-oxide material) can be positioned between the interdigitated electrodes.

As in the examples discussed above, after the electrical circuit pattern 703 is printed onto the substrate 701 it is covered with a coating layer. However, in the example of FIG. 7A, different coating materials are used over the electrodes and over the rest of the printed circuit 703. The first portion of the coating layer 707 covers the entire electrical circuit pattern 703 except for the electrodes and is formed of a material such as, for example, Edragit, Cellulose acetate phthalate (CAP), hydroxypropyl methylcellulose phthalate (HPMCP), polyvinyl acetate phthalate (PVAP), or other materials. In addition to coating and sealing the printed circuit 703, this first portion of the coating layer 707 can also help seal the top surface of the substrate to the bottom surface of the substrate as the substrate is rolled into capsule form. In other implementations, an edible adhesive material is used to "glue" the capsule into its rolled form.

The second portion of the coating layer 709 covers the electrodes of the printed circuit 703 and is formed of an edible material that allows the electrodes to sense the pH of the surrounding environment. For example, the second portion of the coating layer 709 may be formed of gelatin, agar, crosslinked carrageenan, crosslinked guar gum, or other materials.

Figure 7B:
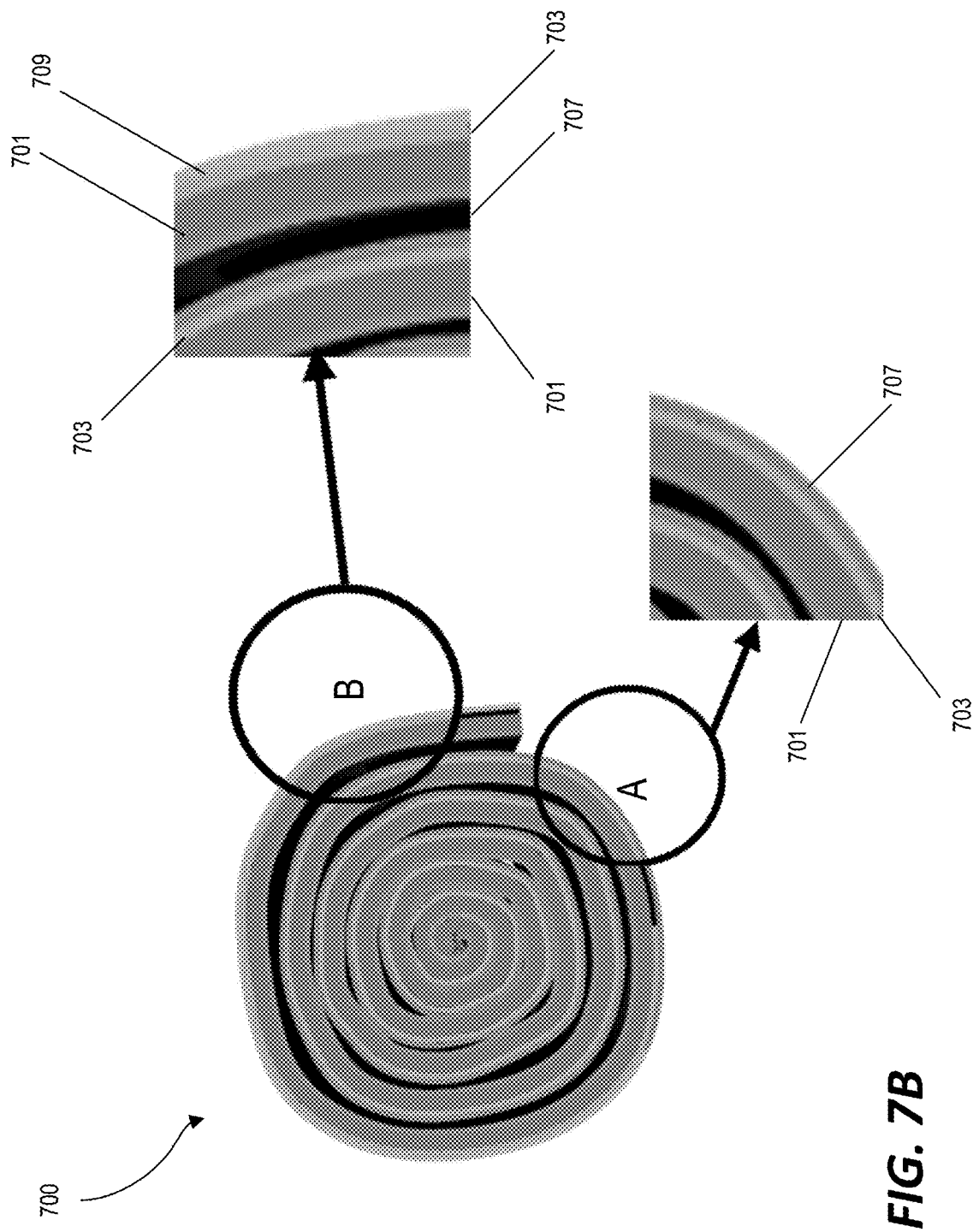
FIG. 7B is a cross-sectional view of the pH sensor of FIG. 7A in its final, rolled form showing the arrangement of the electrodes and the coating layers on the exterior of the pH sensor capsule.

FIG. 7B shows the device 700 of FIG. 7A rolled into capsule form. When the device 700 is rolled, the first portion of the coating 707 that is placed over the printed circuit 703 also contacts the bottom of the substrate 701 in the next layer of the rolled device 700. In this way, the coating can also be used as an adhesive between two adjacent layers in the rolled device. Furthermore, as seen in the insert "A," any exterior portion of the rolled capsule that does not include the electrodes is covered externally with the first portion of the coating 707. However, as seen in the insert "B," the majority of the exterior surface of the rolled capsule—the portion that presents the exterior electrodes of the printed circuit 703—is instead coated with the second portion coating 709 so that the electrodes can react to the surrounding environment.

For implementations in which a material with pH-sensitive impedance properties is positioned near the electrodes, the working mechanism is that for acidic solutions, the $H^+$ residing at the ZnO surface (at the electrodes) can protonate or deprotonate, $ZnO_{(s)} + H_s^+ \Leftrightarrow Zn(OH)^+$ leading to a surface charge and a surface potential, thus it is pH-sensitive. For basic solutions, with increasing $OH^-$ hydroxyl complexes such as $Zn(OH)_3^-$ will appear, $ZnO_{(s)} + 2H_2O \Leftrightarrow Zn(OH)_3^- + H_s^+$. The reaction of ZnO with either acidic or basic solutions will change the impedance between Au and ZnO electrodes, and thus the resonant frequency of the pH sensor changes with the pH value via $$f = \frac{1}{2\pi\sqrt{LC}},$$

where L is the inductance of the antenna (i.e., the coiled "angled portion" that forms the inductor coil in the rolled capsule device) that does not depend on the pH value. To validate and calibrate the edible pH sensor, the pH values of reference solutions were measured via a standard pH meter; the capacitance of the Au—ZnO electrodes were characterized separately; and the resonant frequency of the pH sensor was detected by a circuit including of a reader, a differential amplifier, a signal generator, and an oscilloscope. In the calibration, the edible pH sensors were immersed in standard solutions with pH values from 1 to 12. The capacitance varies with the pH values. Based on the measured pH-dependent capacitance C, the resonant frequency of the pH sensor was calculated using $$f = \frac{1}{2\pi\sqrt{LC}},$$

where L was measured to be 6.1 μH. It is apparent that the calculated resonant frequency agreed with the measured values. The results demonstrate that the edible pH sensor was able to measure the pH value of solutions that are both acidic and basic.

The redox reaction that occurs on the surface of the active materials (e.g, ZnO) affects the capacitance, which is the pseudocapacitive effect. pH values affect redox reactions and thus are reflected by the capacitance. There are many materials, particularly, metal oxides, that exhibit the pseudocapacitive effect. In addition to ZnO, other proton sensitive (and thus pH-sensitive) metal oxides might be utilized, such as $Fe_3O_4$ and $WO_2$.

Figure 8:
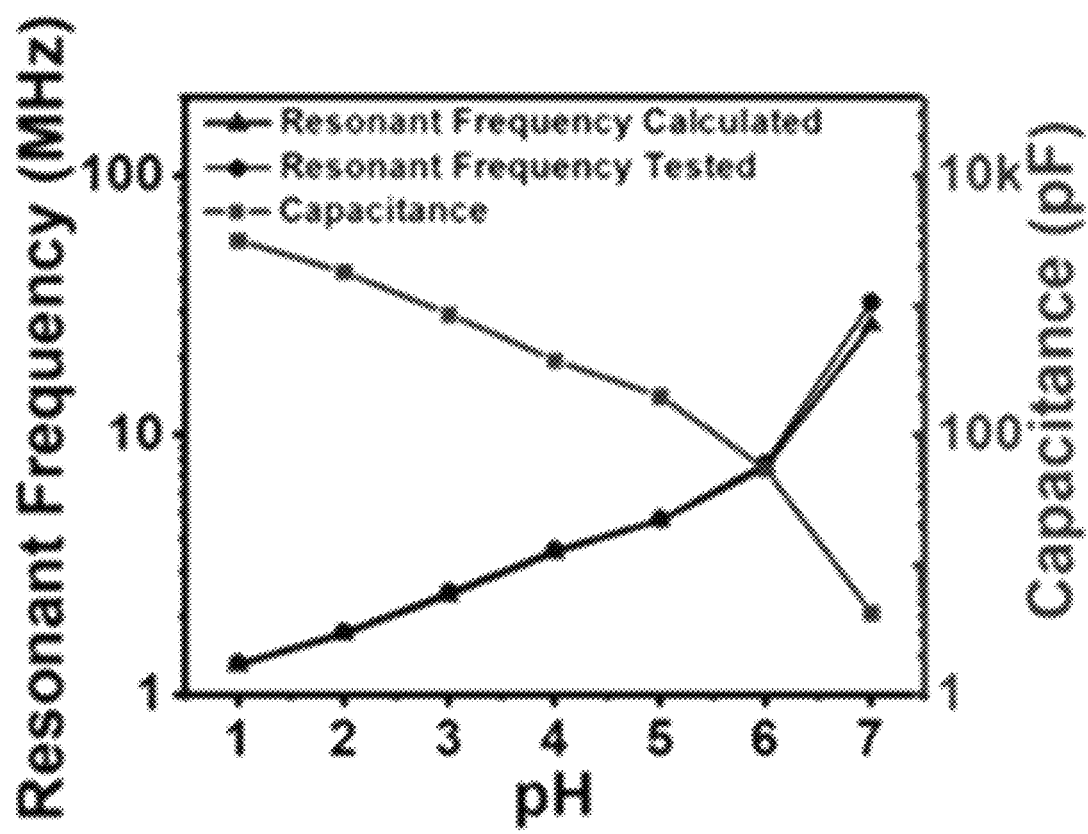
FIG. 8 is a graph illustrating resonance frequencies and corresponding capacitance values measured for pH values ranging from one (1) to seven (7).

In one particular example of the device of FIGS. 7A and 7B, the substrate 701 includes composites with gelatin and glycerol with a thickness of 150 μm. The electrical circuit pattern 703 and the pH-sensitive impedance material 705 (i.e., Au and ZnO, respectively) are deposited on the substrate over the designated area. A thin coating layer of Eudragit 707 is sprayed on top of the printed circuit (without covering the interdigital Au/ZnO sensors). In some implementations, the area of the Au/ZnO electrodes is covered by spraying a Gelatin material 709 while, in other implementations, the Au/ZnO electrode may be left exposed. The substrate is then rolled into the form of a cylindrical capsule and, in some implementations, can be "glued" by spraying another layer of gelatin or other material on the exterior of the rolled capsule and/or providing an area of new Gelatin between the edge of the rolled substrate and the next lower "layer" of the rolled substrate. The final device then has a form factor small enough to be swallowed (smaller than SmartPill™). FIG. 8 illustrates one example of how the resonant frequency and capacitance of the pH sensor 700 changes based on the pH of the surrounding environment.

Gastric residence time is another important factor that determines the value of the swallowable pH-sensor. Typically, the gastric residence time varies from a few minutes for liquids to a few hours for proteins and fats. Thus, during the residence time of foods, the proposed pH sensor can perform real-time measurements of the pH values. In general, the dissolving rate of gelatin composites in acidic environments depends on the solubility of each component and the mass ratio among them. The solubility of gelatin can be modified by different cross-linking agents like glutaraldehyde and formaldehyde. For other components in the composites, adding more plasticizers like glycerol with no solubility in acid environments will decrease the dissolving rate and thus decrease the digestibility, while increasing the portions of materials like Gellan gum will increase the solubility.

Figure 9:
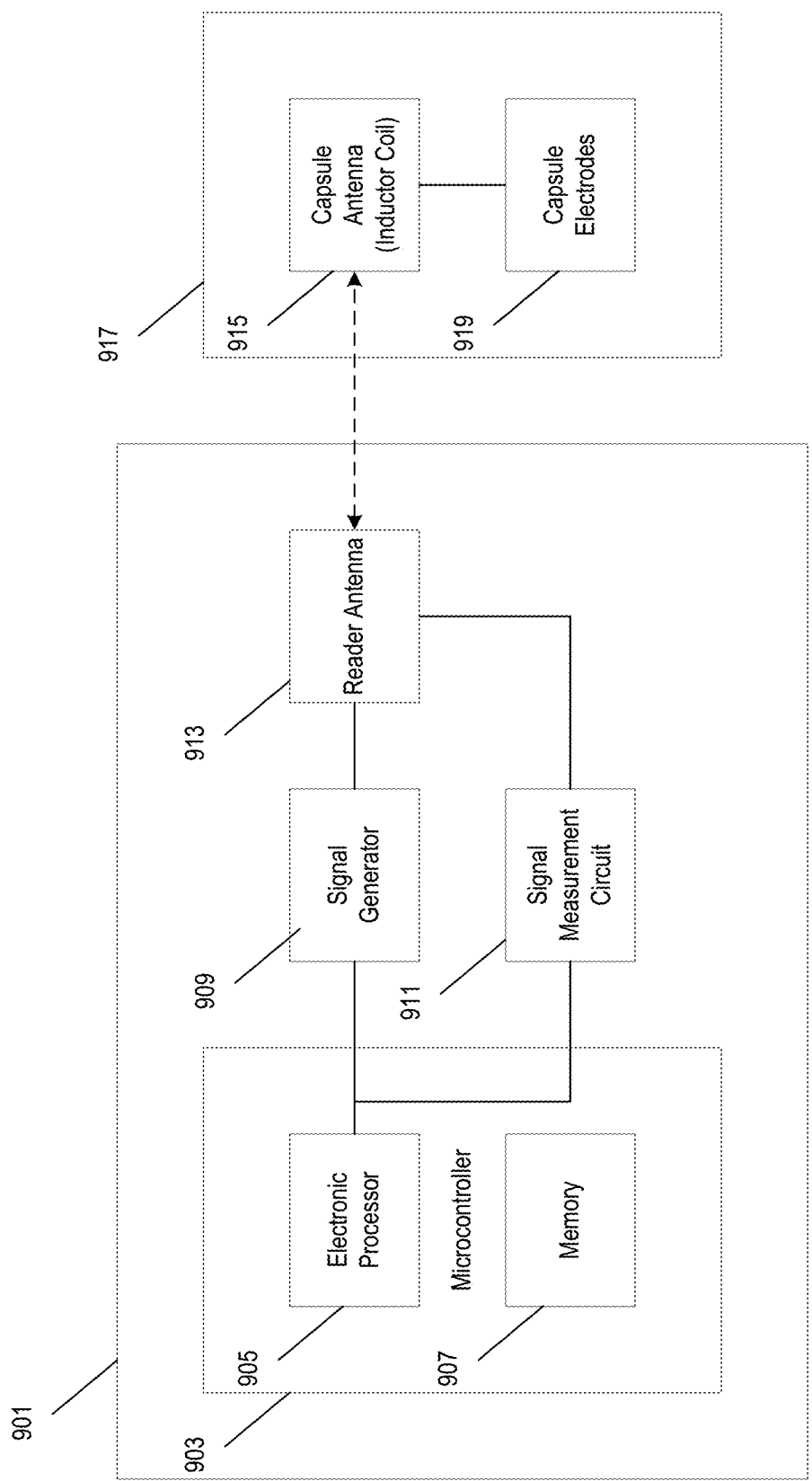
FIG. 9 is a block diagram of an external device in communication with the pH sensor capsule.

FIG. 9 illustrates an example of a control system of an external device for reading the pH sensed by the capsule. The external device 901 includes a microcontroller 903 with an electronic processor 905 and a non-transitory, computer-readable memory 907. In various implementations, the memory 907 may store instructions that are executed by the electronic processor 905 to provide the functionality of the external device 901 and may also store data. The electronic processor 905 is communicative coupled to a signal generator 909 and a signal measurement circuit 911. Both the signal generator 909 and the signal measurement circuit are coupled to a reader antenna circuit 913. The reader antenna 913 of the external device 901 includes an antenna and other matching electrical components (e.g., capacitors) and is configured to communicate with the capsule antenna 915 (i.e., the inductor coil formed by rolling the printed circuit) of the swallowed capsule 917. The signal generator 909 transmits a varying frequency signal to the capsule 917 through the reader antenna and uses the signal measurement circuit 911 to determine the resonant frequency of the capsule 917. As discussed above, the resonant frequency of the capsule 917 will change depending on the pH of the environment chemically interaction with the electrodes 919 of the capsule. Once the resonant frequency is identified, the microcontroller 903 determines the pH value corresponding to the resonant frequency and, in some implementations, stores the determined pH value to the memory 907 or outputs the determined pH value to a display. In some implementations, the controller 903 of the external device 901 is configured to transmit data wirelessly to a smart phone (or other portable computing device)—for example, using Bluetooth and/or WiFi—for easy data communication, processing and display.

Since the electromagnetic wave will penetrate through the tissue and fat on the body, their penetration depth and frequency response can affect how efficient the electromagnetic signal can be coupled between the pH sensor antenna 915 and the reader antenna 913. The reader antenna 913 and corresponding electronics will be placed outside the body but will be as close as possible to the stomach in order to have sufficient signal strength for detection.

Because the sensor capsule is swallowable, edible, and digestible, it can be used to capture multiple repeated pH readings according to a schedule that is, for example, defined for a patient by a medical professional. For example, a patient that reports feeling unwell during the night, but feels better at the doctor's office during the day may be instructed to measure their own gastric pH at multiple times throughout the day. Similarly, a medical professional may want to track variations in gastric pH of a person at hourly increments throughout the day to monitor a condition.

Figure 10:
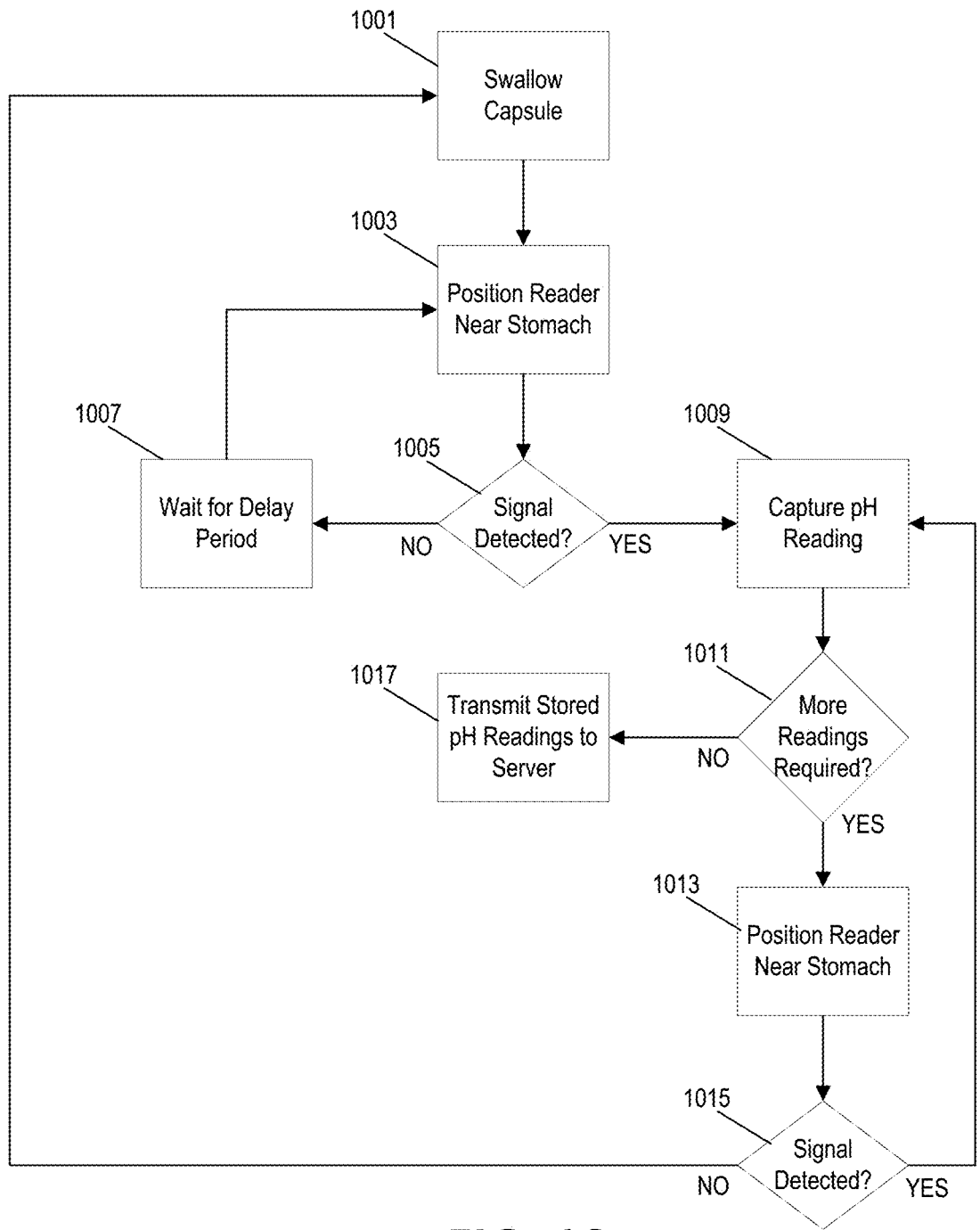
FIG. 10 is a flowchart of a method for capturing multiple pH readings using the sensor system of FIG. 9.

FIG. 10 illustrates one example of a method for capturing multiple pH readings using the system of FIG. 9. First, the user swallows the sensor capsule (step 1001) and positions the external reader on an external body surface near the stomach (step 1003). If a signal is not detected by the external reader (step 1005), the user is instructed to wait for a period of time to allow the swallowed capsule to move from the mouth into the stomach (step 1007). Once a signal is detected, a pH reading is captured (step 1009), for example, by identifying a resonance frequency and/or capacitance of the capsule that corresponds to a particular pH value as discussed above. In some implementations, the pH value is shown to the user as a numeric representation on a graphical user interface (e.g., a smart phone in communication with the external reader). In some implementations, the captured pH value is stored to a memory for later retrieval and use (e.g., to the memory of the smart phone).

After the first pH reading is captured, the user determines whether any more readings are required (step 1011) according to the schedule as defined by the medical professional. If further readings are not required, stored pH readings are transmitted to the server (step 1017). If further readings are required, the user will again place the external reader on a body surface near the stomach at the next time prescribed by the reading schedule (step 1013). If a signal is detected (step 1015), the sensor capsule is still present in the user's stomach and is still operational. The external device then captures another pH reading (step 1009). However, if a signal is no longer detected (step 1015), the sensor capsule has either moved out of the user's stomach along the digestive tract or has been dissolve/digested by the stomach acids to a point where it is no longer functional. Accordingly, when the signal is no longer detected (step 1015), the user will swallow another capsule (step 1001), position the reader near the stomach (step 1003), and wait until a signal is detected with the newly swallowed capsule (step 1005). When the signal of the new sensor capsule is detected (step 1005), another pH reading is captured (step 1009).

As discussed above, in some implementations, the external reader is configured to communicate with a device such as, for example, a smart phone. In other implementations, the external reader may be incorporated into the device itself (e.g., as part of the smart phone) or may be configured to include its own internal mechanism for wireless communication with a remote server (e.g., a WiFi or cellular communication device). In some such implementations, the external reader and/or the device to which the external reader is in communication (e.g., a smart phone) is configured to automatically transmit stored pH readings to a remote server. In some implementations, the device is configured to transmit all of the stored pH readings after all of the required pH readings have been captured and recorded (as illustrated in the example of FIG. 10). In other implementations, the device may be configured to transmit a pH reading to the remote server after each individual pH reading is captured or according to a defined periodic schedule (e.g., every 2 hours, the device transmits all stored pH readings to the server (or all pH readings that have not been previously transmitted to the server)).

In some implementations, the system is configured to provide the transmitted pH readings to a system that is accessible by the medical professional that has requested the pH readings. For example, a doctor treating a patient can automatically receive the pH readings from the patient without requiring a follow-up visit or additional steps for reporting the captured pH readings.

When the schedule for capturing pH readings is defined, a medical professional (or a computer system) may be able to predict how many sensor capsules will be needed in order to capture the requested pH readings according to the defined schedule (based, for example, on an initial measured gastric pH and an estimated amount of time for the capsule to dissolve). Accordingly, a medical professional can, in some implementations, provide the user with a plurality of sensor capsules along the external reader device and the defined schedule for capturing pH readings.

Furthermore, in some implementations, the external reader device and/or another user device may be configured to provide reminders/instructions to a user for performing the method of FIG. 10 and/or may be configured to automatically perform some functional steps (such as those illustrated in FIG. 10). For example, in an implementation where the external reader device is in communication with a smart phone, the smart phone may be configured to (1) receive the defined pH reading schedule for a particular user, (2) display notifications reminding the user to capture a pH reading, (3) display to the user an indication of whether a signal is detected, to display to the user an instruction to swallow another sensor capsule, (4) display to the user an indication of the measured gastric pH, and/or (5) automatically transmit pH readings to a remote server (e.g., to the prescribing medical professional).

Although the examples described above focus on the use of a swallowable capsule that moves through the digestive tract, other implementations of the systems and methods described herein are also possible. For example, the antenna 915 and electronics 919 described in the examples above may be integrated on a flexible platform that can be attached to the skin in the epigastrium will be explored. It has been demonstrated the capability for such integration of an antenna-like RF structure onto a flexible polyimide substrate that maintains the desired frequency response. Other configurations of the antenna integration with electronics to achieve a minimum footprint yet optimal signal strength and pH value readout are also possible.

Furthermore, although the example discussed above describe the substrate as rolled into a "cylindrical" form, other final forms are also possible.

Therefore, the invention provides, among other things, a system for measuring pH in a biological environment that includes a substrate with an electrical circuit pattern printed thereon and rolled in such a way that the printed circuit forms an inductor coil that operates as a wireless communication antenna. Various features and advantages of the invention are set forth in the following claims.

What is claimed is:

1. A method of assembling a swallowable pH sensor, the method comprising:
    providing a substrate;
    printing an electrical circuit pattern on a top surface of the substrate, the electrical circuit pattern including a plurality of interdigitated electrodes, and an antenna portion; and
    rolling the substrate into a cylindrical form, wherein the plurality of interdigitated electrodes are positioned on an outermost layer of the rolled substrate and wherein the rolling of the substrate causes the antenna portion of the electrical circuit pattern to form a coil shape;
    wherein printing the electrical circuit pattern on the top surface of the substrate includes printing:
        a first plurality of linear electrodes arranged in parallel and coupled to a first node line extending perpendicular to the first plurality of linear electrodes,
        a second plurality of linear electrodes arrange in parallel, interdigitated with the first plurality of linear electrodes and coupled to a second node line extending perpendicular to the second plurality of linear electrodes,
        a linear portion extending from the first node line, and
        an angled portion extending from the second node line to a distal end of the linear portion to form an angle between the linear portion and the angled portion.

2. The method of claim 1, wherein the substrate provided is formed of a gelatin-based material that includes a plasticizer to increase flexibility of the substrate.

3. The method of claim 1, wherein printing the electrical circuit pattern on the top surface of the substrate includes using a gold material to print the electrical circuit pattern on the top surface of the substrate.

4. The method of claim 1, further comprising coating at least part of the top surface of the substrate with a coating layer after printing the electrical circuit pattern on the top surface of the substrate.

5. The method of claim 4 wherein the coating layer acts as an adhesive to couple the top surface of the substrate to a bottom surface of the substrate in layers as the substrate is rolled into the cylindrical form.

6. The method of claim 4, wherein coating at least part of the top surface of the substrate with the coating layer includes coating portions of the top surface of the substrate that do not include the plurality of electrodes with a first coating layer material.

7. The method of claim 6, wherein rolling the substrate into the cylindrical form includes rolling the substrate so that the plurality of electrodes are positioned on the outermost layer of the rolled substrate without any coating layer covering the plurality of electrodes.

8. The method of claim 6, wherein coating at least part of the top surface of the substrate with the coating layer includes coating a portion of the top surface that includes the plurality of electrodes with a second coating layer material.

9. The method of claim 1, wherein printing the electrical circuit pattern on the top surface of the substrate includes printing:
- a linear offset portion extending from the second node line in a direction parallel with the second plurality of linear electrodes, wherein the angled portion extends from a distal end of the linear offset portion to the distal end of the linear portion to form a substantially triangular pattern.

10. The method of claim 9, wherein printing the electrical circuit pattern on the top surface of the substrate includes printing a capacitor formed on the linear offset portion.

\* \* \* \* \*